United States Patent
Gustafson et al.

[11] Patent Number: 5,425,738
[45] Date of Patent: Jun. 20, 1995

[54] ENDOSCOPIC ANASTOMOSIS RING INSERTION DEVICE AND METHOD OF USE THEREOF

[75] Inventors: Scott B. Gustafson, Nanuet, N.Y.; Frederick Ahari, Newton, Mass.; William J. Allen, Stratford, Conn.; George Jessup, Strathfield, Australia; John F. Howard, Brookfield, Conn.; Harold S. Terk, Stamford, Conn.; Lester F. Miller, Danbury, Conn.

[73] Assignee: American Cyanamid Company, Wayne, N.J.

[21] Appl. No.: 139,602

[22] Filed: Oct. 18, 1993

Related U.S. Application Data

[63] Continuation-in-part of Ser. No. 90,433, Jul. 6, 1993, abandoned, which is a continuation of Ser. No. 865,235, Apr. 19, 1992, abandoned.

[51] Int. Cl.[6] ................................ A61B 17/00
[52] U.S. Cl. ........................ 606/153; 606/151
[58] Field of Search ........... 606/151, 153, 154, 157, 606/158, 213, 215, 216, 218; 227/175, 178, 179, 181, 19

[56] References Cited

U.S. PATENT DOCUMENTS

| | | | |
|---|---|---|---|
| 4,667,673 | 5/1987 | Li | 606/153 |
| 4,907,591 | 3/1990 | Vasconcellos et al. | 606/154 |
| 4,957,499 | 8/1990 | Lipatov et al. | 606/153 |
| 4,964,863 | 10/1990 | Kanshin et al. | 606/153 |
| 5,197,649 | 3/1993 | Bessler et al. | 227/179 |
| 5,234,447 | 8/1993 | Kaster et al. | 606/151 |
| 5,236,437 | 8/1993 | Wilk et al. | 606/158 |
| 5,275,622 | 1/1994 | Lazarus et al. | 606/153 |

FOREIGN PATENT DOCUMENTS

| | | | |
|---|---|---|---|
| 552050 | 7/1992 | European Pat. Off. | A61B 17/00 |
| 540010 | 5/1993 | European Pat. Off. | A61B 17/115 |

Primary Examiner—Stephen C. Pellegrino
Assistant Examiner—Jeffrey A. Schmidt
Attorney, Agent, or Firm—C. F. Costello, Jr.; M. W. Smith

[57] ABSTRACT

An endoscopic insertion device for inserting an anastomosis ring having two unitary members in an anatomic tubular body member comprises an anastomosis ring adapter for mounting the unitary members in an engaging position, an inserter for inserting the ring adapter in the tubular body member, and an actuator for actuating the adapter to close the anastomosis ring. A method of using the endoscopic insertion device includes the steps of inserting the anastomosis ring in an engaged position into the tubular body member, securing opposite ends of the tubular body member to the engaged anastomosis ring, applying a biasing force to close the anastomosis ring, releasing the biasing force, and axially withdrawing the insertion device from the closed anastomosis ring.

17 Claims, 18 Drawing Sheets

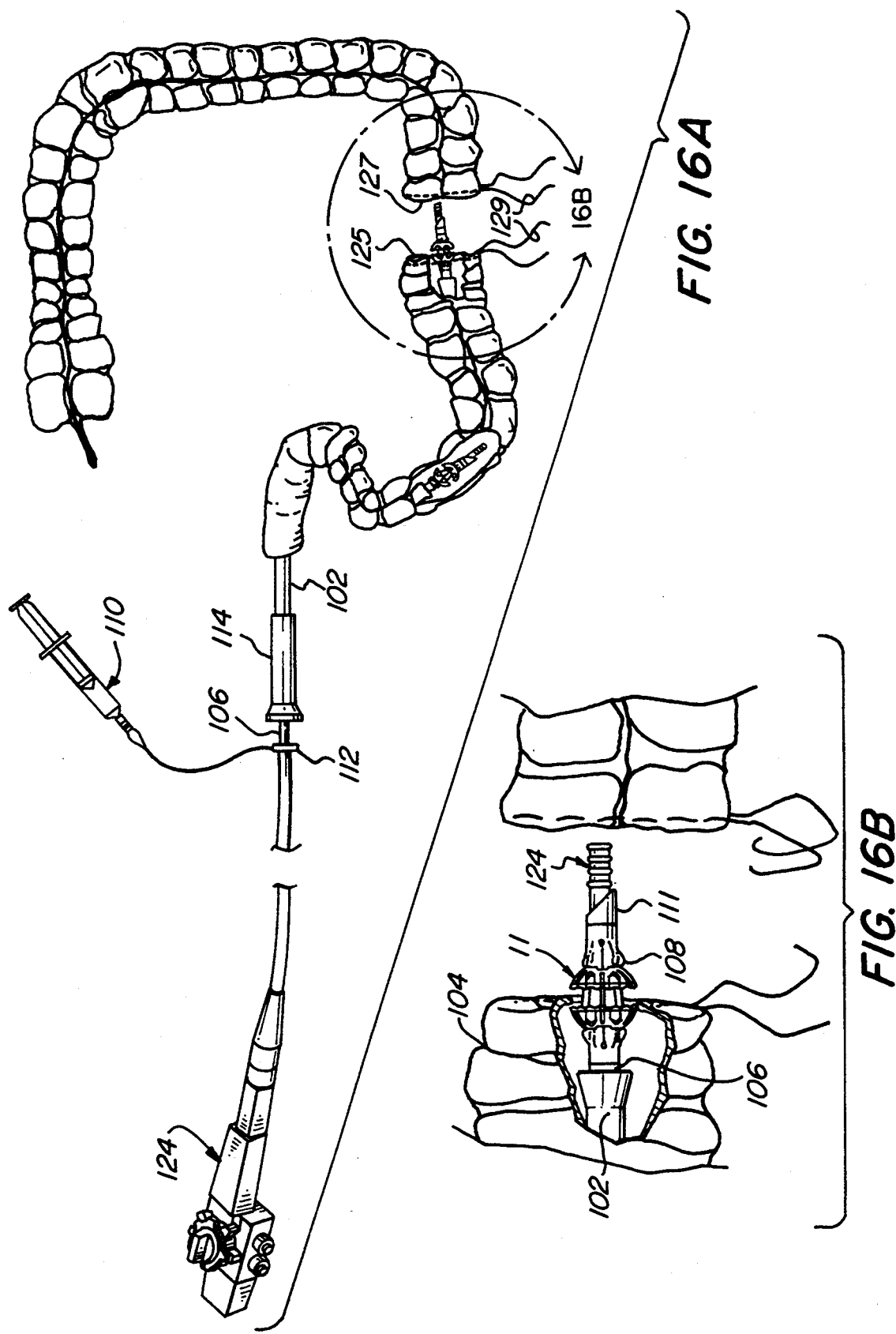

ENDOSCOPIC ANASTOMOSIS RING INSERTION DEVICE AND METHOD OF USE THEREOF

This application is a continuation-in-part of U.S. patent application Ser. No. 08/090,433, filed Jul. 6 1993, abandoned, which is a continuation of U.S. patent application Ser. No. 07/865,235, filed Apr. 8, 1992, now abandoned.

BACKGROUND OF THE INVENTION

1. Field of the Invention

This invention relates to a surgical device, and more particularly to an anastomosis ring insertion device for use in anastomosing tubular body members.

The insertion device of the subject invention inserts the anastomosis ring into the human body using a non-invasive surgical procedure. Such a procedure entails inserting the anastomosis ring through a natural body orifice. The non-invasive procedure has several advantages over invasive surgery, which inserts the anastomosis ring through a bodily incision proximate to the severed ends of the body organ, such as quicker healing time, less patient trauma and reduced risk of infection for the patient.

The subject invention can be used, for example, to anastomose the esophagus by inserting the anastomosis ring through the mouth. As another example, the insertion device of the subject invention can insert the anastomosis ring through the anal orifice of the patient to anastomose the lower colon, or bowel section, of the intestines.

After a surgical procedure such as cutting and removing a diseased or cancerous portion of a tubular body member, the severed ends of the body organ must be anastomosed. Several procedures are available for connecting together two sections of hollow tubular body members such as the intestines. Known procedures include suturing, stapling or clamping the severed ends together. For example, U.S. Pat. Nos. 4,576,167; 4,603,693 and 4,646,745 are directed to circular surgical staplers for joining hollow body organs.

Another procedure using anastomosis buttons and clamps is disclosed in U.S. Pat. Nos. 3,771,526, 4,055,186 and 4,154,241. These devices may utilize inserter rods which are forced upwardly into the rectum through the anus to position one half of a clamp device in the lower colon and engage the other half of the clamp device positioned in the upper colon to draw the two halves together.

Still another procedure involves use of an anastomotic device that is the subject of U.S. Pat. Nos. 4,467,804, 4,552,148 and 4,766,898, which are assigned to the assignee of the present application, and marketed and sold under the VALTRAC® trademark. The insertion device of the subject invention is used in conjunction with an anastomotic device of the type disclosed in these patents. The anastomotic device receives the open ends of two tubular body members to be anastomosed over a pair of ring members. The ring members have annular connecting means which mate with each other to clamp the body organs contiguous to each other so they can grow and heal together.

The anastomotic device, which will be referred to hereinafter and in its embodiment for use with the subject invention as an anastomosis ring, is pictured in FIGS. 7 through 9. A complete anastomoses ring 11 is shown in FIG. 7 and is comprised of two identical unitary members 13 of mushroom cap configuration. FIGS. 8 and 9 show a bottom plan view and a top plan view, respectively, of the unitary member. The bottom plan view in FIG. 8 shows a ring member 15 having a pair of diametrically opposed depending legs 17 each supporting a plurality of engaging pawls 19. Alternately positioned between the depending legs and opposite to each other are depending engaging members 21, each of which has a pawl engaging recess 23 to cooperatively receive the pawls when the two unitary members 13 are joined together to form the anastomosis ring. For ease of reference, the ring member will be referred to as the head of the anastomosis ring and the depending legs and engaging members will be referred to as the neck.

FIG. 9 shows the top of the unitary member molded to form four notches 25 and four ridges 27 alternately positioned around its inner periphery.

As shown in FIG. 7, the pawls 19 are positioned on each depending leg 17 such that the unitary members can mate in an engaged position as shown in solid lines, or in a fully closed position as shown in solid and broken lines. As will be discussed in greater detail below, the unitary members are mounted on the insertion device of the subject invention in the engaged position and then inserted into the body. A profile of the engaging pawl showing engaging edge 29 and slope 31 can also be seen in FIG. 7.

The unitary members 13 are formed of a bio-absorbable bio-fragmentable material that permits disintegration of the device in a relatively short period of time after healing of the tubular body member ends begins. Acceptable materials for forming the anastomosis rings are disclosed in U.S. Pat. No. 3,297,033 and are referred to as poly-hydroxyacetic ester and lactide copolymers. Molded surgical articles made from a wide variety of glycolide/lactide copolymers are well known in the art.

2. Description of the Prior Art

U.S. Pat. No. 4,667,673, also assigned to the assignee of the present application, discloses an applicator device for mounting and inserting the anastomosis ring in a bowel section of the patient and a method for using the applicator. The device includes a mounting extension for mounting the two halves of the anastomosis ring and an inserter which may be curved. The two halves are spaced apart from each other in the mounted position and then drawn together by manipulation of the inserter. The inserter portion of the applicator passes through the interior of the rectum and out through the exterior of the anus so that the placement of the anastomosis ring can be done without being exposed to the dirty and contaminated end of the bowel.

European Patent Publication No. 540,010, published May 5, 1993, discloses a clamping device for approximating and joining two ends of tubular tissue. First and second clamping members are purse-string sutured to opposing open ends of a tubular body member. The first clamping member includes a ratchet-surfaced central shaft and an actuating shaft. A cable is attached to the second clamping member and extends through the actuating shaft to be pulled by a surgeon/user to draw the second clamping member toward the ratchet-surfaced central shaft of the first clamping member to close the gap between the clamping members and compress together the open ends of the tubular body member. The cable is cut by a blade on the actuating shaft, which is then withdrawn axially from the body. The publication discloses use of the VALTRAC® anastomosis ring as an alternative to the first and second clamping members.

SUMMARY OF THE INVENTION

It is a principal object of the present invention to improve upon and enhance an applicator insertion device for surgically inserting an anastomosis ring.

Accordingly, it is an object of the invention to provide an insertion device for surgically inserting an anastomosis ring in a tubular body member, or organ, through a natural body orifice.

It is a further object of the invention to provide an insertion device that swiftly and easily mates the unitary members of the anastomosis ring to clamp the open ends of the body member in a contiguous manner.

It is still a further object of the invention to provide an insertion device that quickly releases a mounting adapter from the anastomosis ring and withdraws the adapter through a natural body orifice.

It is yet a further object of the invention to provide a safe, easy to use method for surgically inserting the anastomosis ring in a tubular body member through a natural orifice.

As a further improvement in an applicator device for inserting an anastomosis ring, the present invention is directed to an endoscopic insertion device and provides advantages for mounting and inserting the anastomosis ring in, for example, the esophagus or the intestines using a non-invasive surgical procedure.

These and other objects are achieved by the endoscopic insertion device of the present invention, which in one aspect comprises anastomosis ring adapter means for mounting two unitary members in an engaged position, inserting means for inserting the adapter means in a tubular body member, and actuating means for actuating the adapter means to close the anastomosis ring and release the adapter means from the anastomosis ring.

In another aspect of the invention, an endoscopic insertion device for inserting an anastomosis ring having two unitary members into a tubular body member comprises an anastomosis ring adapter having a cylindrical collar, a sliding cage mounted for axial movement within the collar, and a spool mounted for axial movement within the sliding cage. An endoscope having a biopsy port is connected at its distal end to the collar, and a handle assembly is connected to a proximal end of the endoscope and includes a pivotable trigger. In addition, a control rod is connected at a first end to the trigger and at a second end to the spool.

In yet another aspect of the invention, an endoscopic insertion device comprises an elongated hollow outer sleeve and an inner obturator extending through the outer sleeve and having an inflatable cuff at its distal end. The cuff may be fluid or gas filled and may require up to 10 atmospheres of pressure to be fully inflated or actuated. The inflatable cuff is used to convey the anastomosis ring in an engaged position protected from premature closure through the tubular body member, close the anastomosis ring and release the obturator from the closed anastomosis ring so it may be withdrawn axially from the body. The cuff may be used as a luminal dilator or measuring device.

In accordance with another aspect of the invention, a method for inserting an anastomosis ring having two unitary members into a tubular bodymember uses an endoscopic insertion device having an anastomosis ring adapter and an actuator. The method comprises the steps of inserting the unitary members in an engaged position into the tubular body member, applying a biasing force to the anastomosis ring to close the anastomosis ring, releasing the biasing force, and axially withdrawing the anastomosis ring adapter from the closed anastomosis ring.

In accordance with yet another aspect of the invention, a method for inserting an anastomosis ring having two unitary members into an anatomic tubular body member uses an endoscopic insertion device having an outer sleeve and an inner obturator with an inflatable cuff. The method comprises the steps of positioning the anastomosis ring in an engaged position on, the cuff, partially inflating the cuff to limit axial movement of the anastomosis ring, inserting the cuff and anastomosis ring into the tubular body member, securing the open ends of the tubular body member to the anastomosis ring, deflating the cuff and advancing the obturator to position the cuff distally from the anastomosis ring, inflating the cuff, axially sliding the outer sleeve and inner obturator relatively toward each other to squeeze the anastomosis rinng between the inflatable cuff and the stop and close the anastomosis ring, deflating the cuff, and axially withdrawing the In accordance with still another aspect of the invention, a method for closing the anastomosis ring is to use the hydraulic action of the cuff to act as a piston and push against the cap of the anastomotic ring. This allows for closure of the anastomotic ring without the need for a push-pull mechanism. Multiple cuffs may be used to achieve this affect. These cuffs may be attached directly to the insertion tube of an endoscope to allow insertion, closing, and release of an anastomotic ring with or without a hollow outer sleeve or an inner obturator.

These and other objects, aspects, features add advantages of the present invention will become apparent from the following detailed description of the preferred embodiment taken in conjunction with the drawings.

BRIEF DESCRIPTION OF THE DRAWINGS

FIG. 16A is an isolated view of a tubularly body member with the endoscopic insertion device of the second embodiment inserting an anastomosis ring therein; and FIG. 16B is an enlarged view of opposite open ends of the tubular body member receiving the anastomosis ring as shown in FIG. 16A.

DESCRIPTION OF THE PREFERRED EMBODIMENTS

Figure 1:
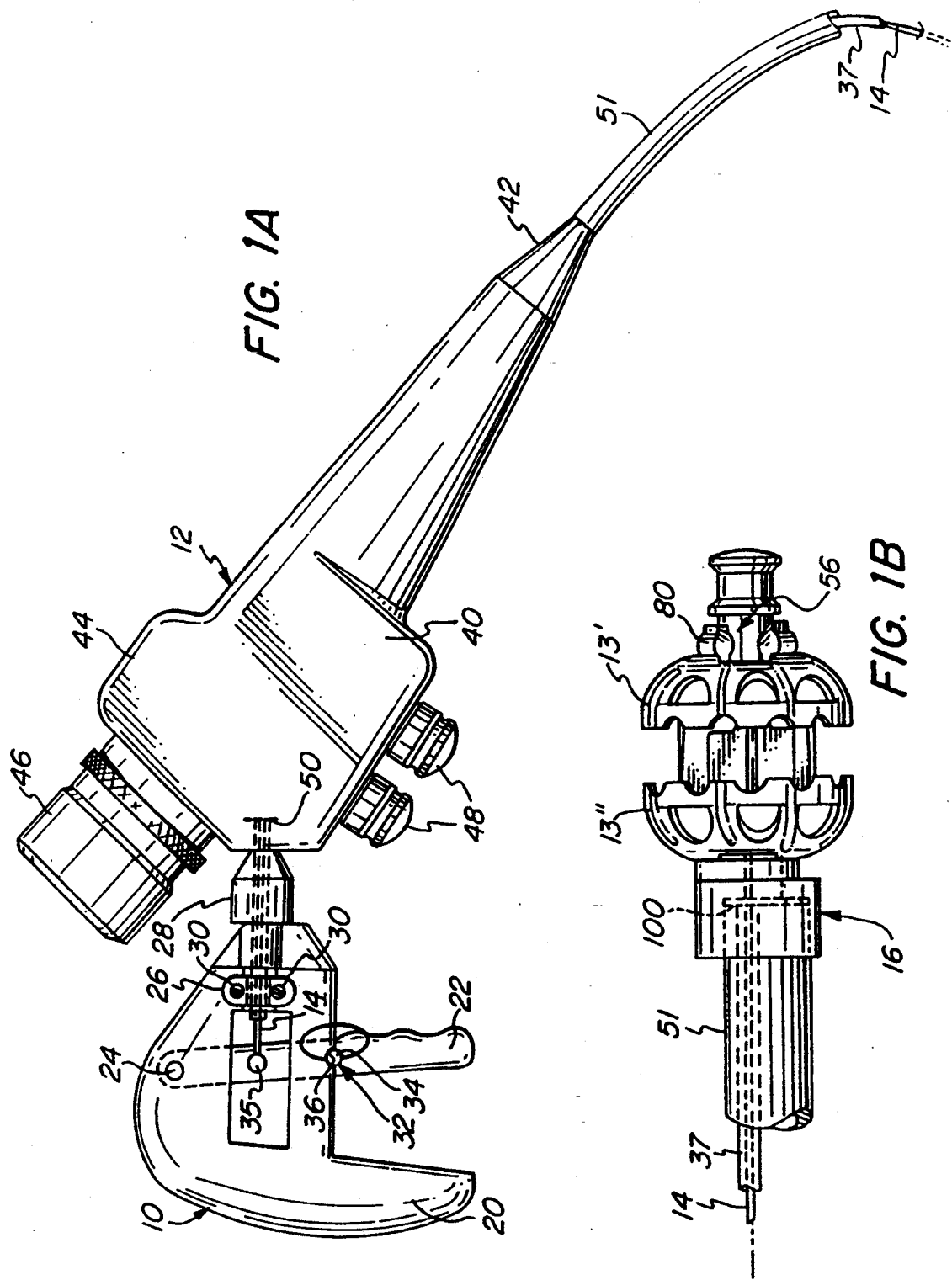
FIG. 1A is a side view of an endoscope with an attached handle assembly in accordance with a first embodiment of the present invention.
FIG. 1B is a side view of an adapter with an anastomosis ring mounted ready for use in accordance with the first embodiment of the present invention.

FIGS. 1 through 6 illustrate in detail an endoscopic anastomosis ring insertion device in accordance with a first embodiment of the invention, FIGS. 1A and 1B illustrate the three main components of the endoscopic anastomosis ring insertion device, FIG. 1A shows a handle assembly 10 and an endoscope 12, The handle assembly is connected to a proximal end of the endoscope and actuates a control cable 14, The control cable extends through the endoscope and is connected to an anastomosis ring adapter 16, The control cable includes a spherical fastener 35 at each end and has a control cable sheath 37 extending substantially the entire length of the control cable. The ring adapter is shown generally in FIG. 1B with an anastomosis ring mounted thereon in the engaged position, The anastomosis ring is formed from the engagement of a distal unitary member 13' and a proximal unitary member 13".

As used herein, the term "distal" will refer to that part of the device which is furthest away from the surgeon-user, and the term "proximal" refers to that part of the device which is closest to the surgeon-user.

The handle assembly shown in FIG. 1A comprises a handle body 20 and a trigger 22 pivotably mounted on a pivot pin 24. The control cable is connected to the trigger and passes through a guide clamp 26 and cable adapter 28 in the handle assembly. The guide clamp provides a passageway 39 for receiving the control cable and is secured to the handle body by, for example, screws 30. The cable adapter connects the handle assembly with the endoscope to form a single unit.

The handle also includes a locking mechanism 32 for locking the trigger. The locking mechanism includes a locking pin 34 that can be inserted through a locking hole 36 in the trigger to engage a locking notch 38 in the handle body and prevent the trigger from pivoting about the pivot pin 24. The locking hole, the locking notch and the locking pin are best seen in FIG. 4B.

The endoscope 12 shown in FIG. 1A is, per se, known in the art. The endoscope typically includes an elongated body 40 with a distal end 42 and a proximal end 44. At the proximal end is an eye-piece 46 and control knobs 48. Alternatively, the endoscope may be equipped to provide images of the patient electronically. The control knobs are used to control and manipulate, for example, a light cable and an optical cable running through the endoscope. An endoscopic guide 51 extends from the distal end of the elongated body to provide a passageway for the control cable and any other cables in the endoscope. The control cable and sheath enter the endoscope through a biopsy port 50 and extend through the endoscopic guide. As shown in FIG. 1B, a large washer 100 fits flush on the distal end of the endoscopic guide to restrain passage of the control cable sheath.

Figure 2:
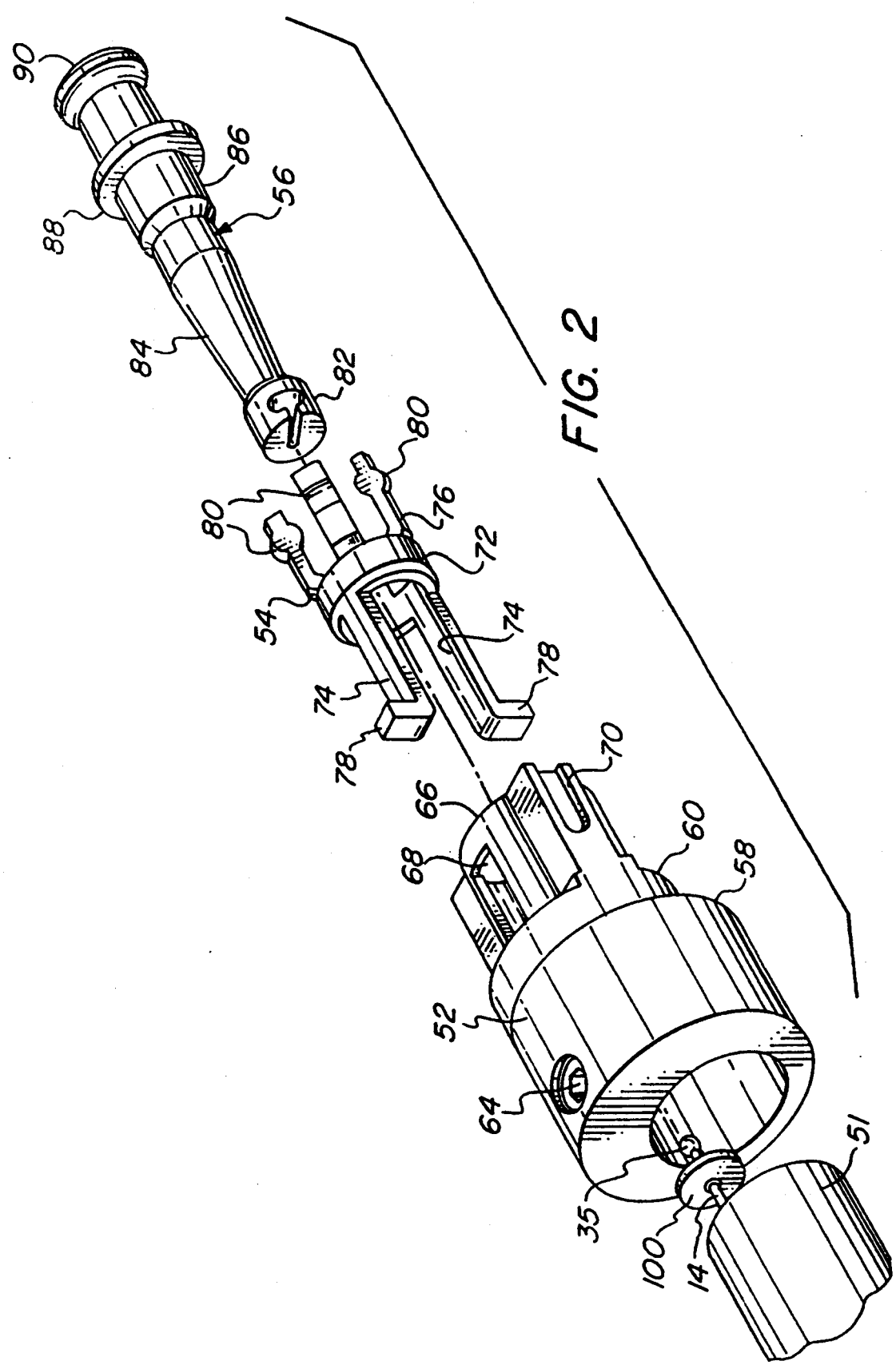
FIG. 2 is an exploded view, in perspective, of the adapter in accordance with the first embodiment of the present invention.
Figure 3:
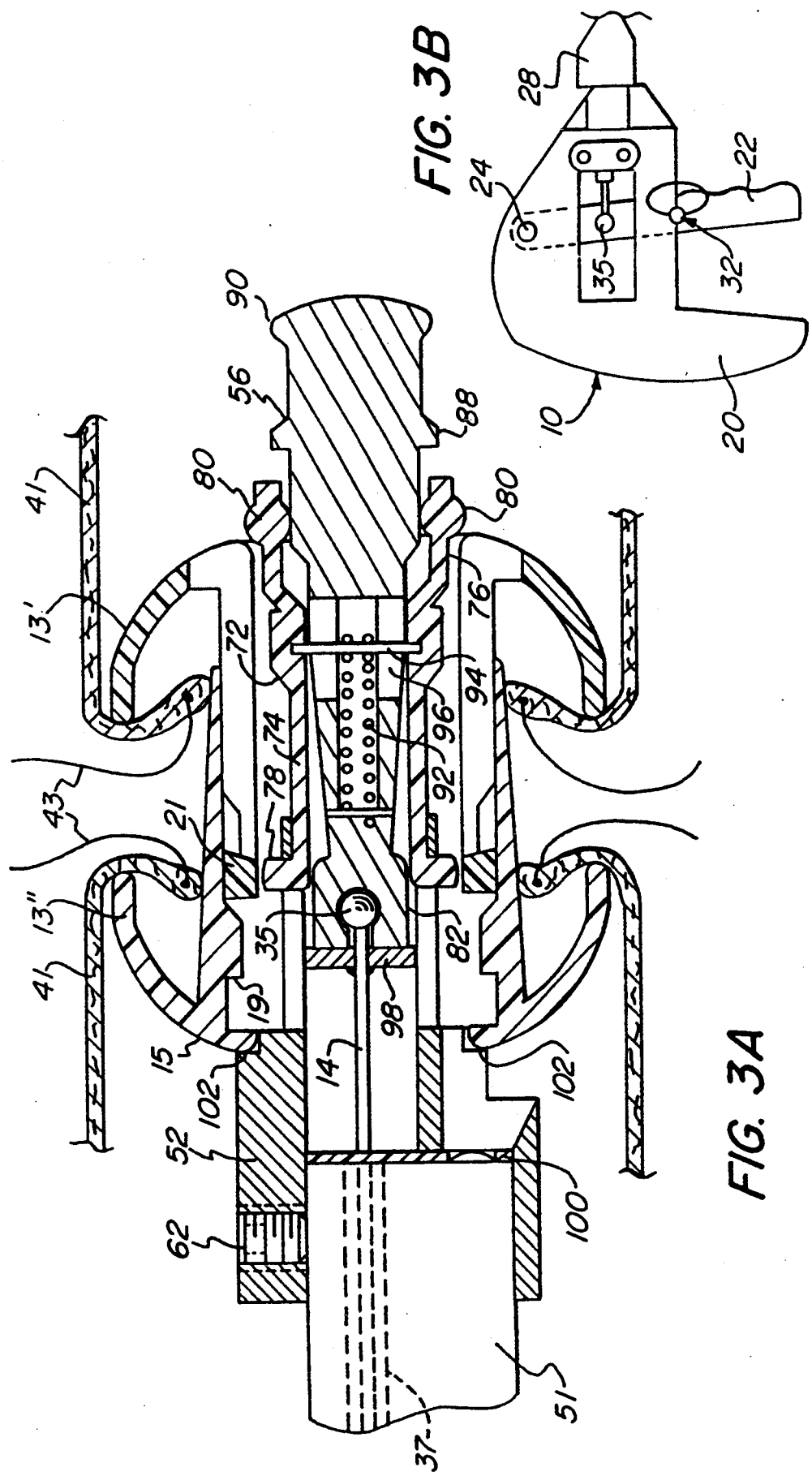
FIG. 3A is a cross-sectional side view of the adapter with the anastomosis ring in an "open" position in accordance with the first embodiment of the present invention.
FIG. 3B is a side view of the handle assembly locked in the "open" position in accordance with the first embodiment of the present invention.
Figure 4:
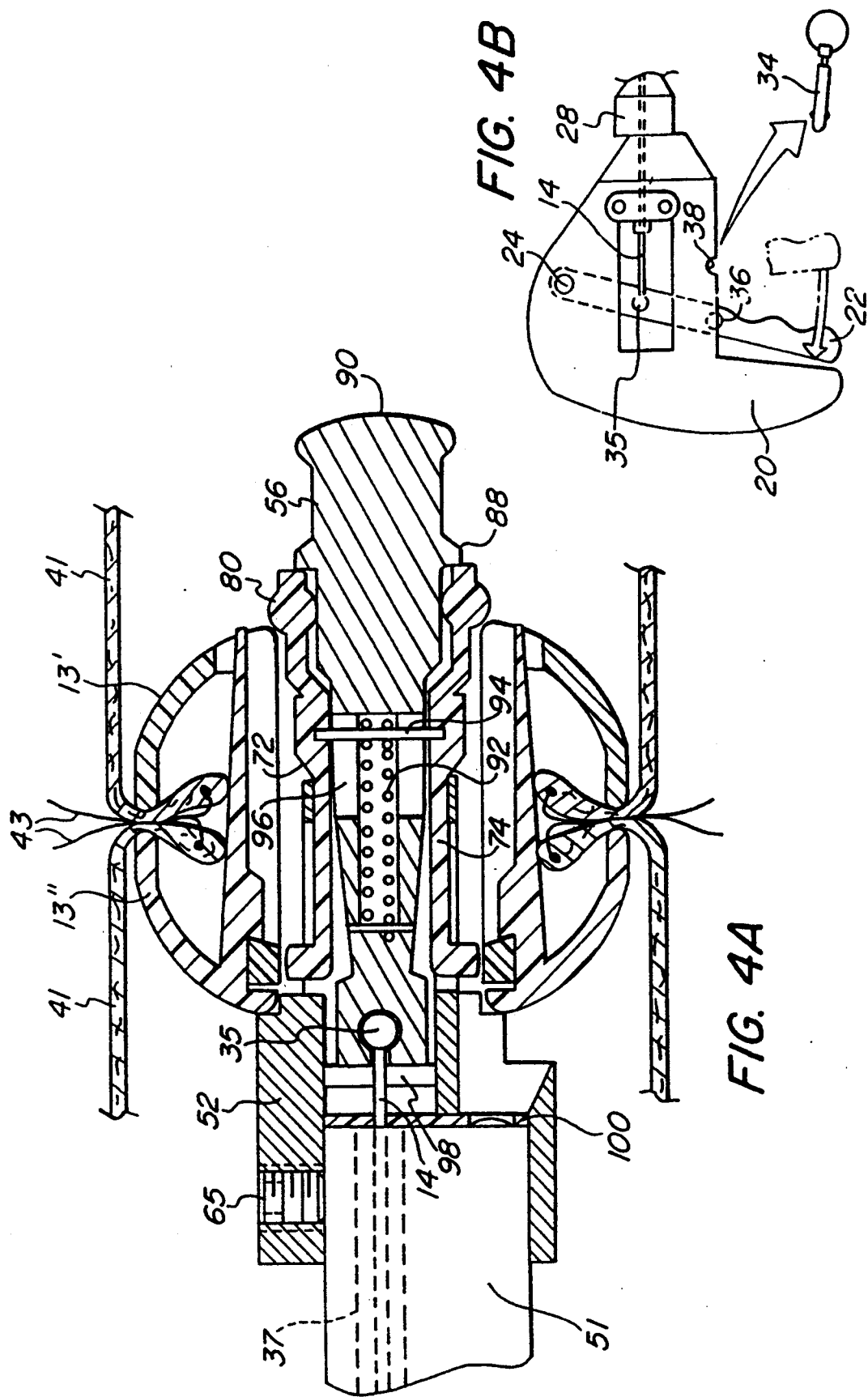
FIG. 4A is a cross-sectional side view of the adapter with the anastomosis ring in a "closed" position to clamp the open ends of the body organ together in accordance with the first embodiment of the present invention.
FIG. 4B is a side view of the handle in the "closed" position in accordance with the first embodiment of the present invention.
Figure 5:
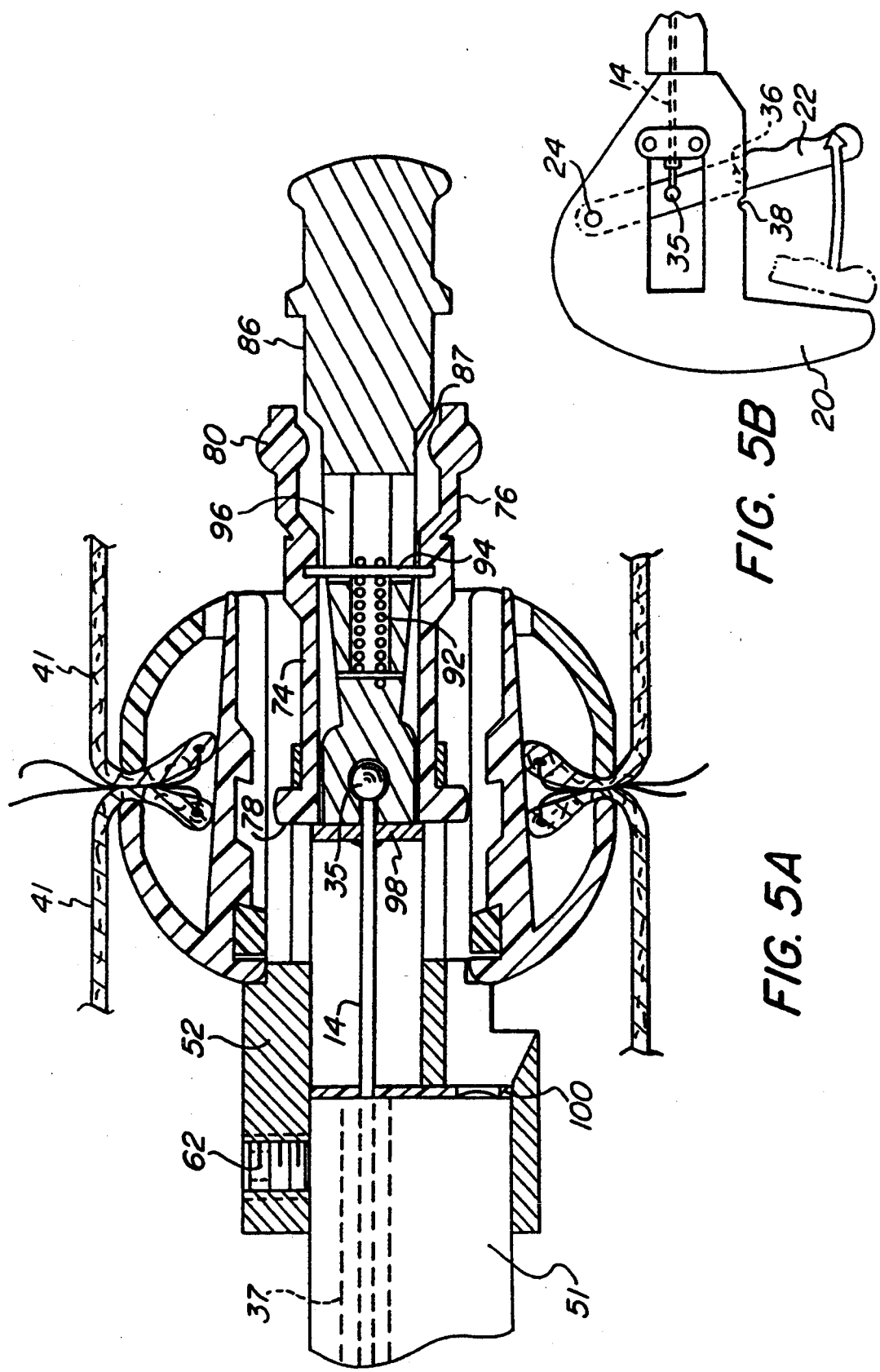
FIG. 5A is a cross-sectional view of the adapter in the "release" position in accordance with the first embodiment of the present invention.
FIG. 5B is a side view of the handle in the "release" position in accordance with the first embodiment of the present invention.

With reference to FIGS. 2 and 3A, the anastomosis ring adapter 16 comprises generally a cylindrical collar 52, a sliding cage 54 and a spool 56. The collar has a main section 58 and a secondary section 60 of a reduced diameter. The main section is secured to the distal end of the endoscopic guide by a bolt 62, or other fastening means, extending through a transverse opening 64 in the main section.

The secondary section has a hollow sleeve 66 for receiving the cage. The sleeve includes two diametrically opposed elongated slots 68. Two diametrically opposed elongated notches 70 are positioned between the slots.

The sliding cage has an annular rim 72 with two sliding fingers 74 extending in a first axial direction and a plurality, such as four, containing fingers 76 extending in a second axial direction opposite to the first direction. Each sliding finger includes an upturned lip 78 that slides within one of the elongated slots 68 in the hollow sleeve. Each containing finger includes an enlarged contact point 80 for contacting the anastomosis ring and the spool in a manner that will be described below. The contact point shown in the figures is circular in shape.

The spool is formed to have a proximal end 82, a truncated cone section 84 and a distal cylindrical section 86. The cylindrical section has an abutting annular ring 88 formed thereon and a rounded knob-shaped end 90 for easing the insertion device through the tubular body member. The spool also includes an internal spring 92 for biasing the spool relative to the sliding cage. The spring is connected at its free end to a transverse pin 94 which extends through elongated slots 96 in the spool and is anchored in the annular rim of the cage. The spool is connected at its proximal end to the control rod by the distal spherical fastener 35 and a small washer 98. As shown, for example, in FIG. 3A, the small washer is secured flush against the proximal end. The control rod is manipulated by the handle assembly to slide the spool back and forth within the collar and the cage.

Before the endoscopic insertion device is inserted into the body, the anastomosis ring is mounted on the adapter in the engaged position as shown in FIG. 1B. In this position, the head of the proximal unitary member 13″ rests against a shoulder 102 on the collar and is prohibited thereby from moving in a first direction toward the proximal end of the insertion device (see FIG. 3). Likewise, the distal unitary member 13′ is prohibited from moving in a second direction toward the distal end of the insertion device by engagement of the head with the enlarged contact points 80 on the containing fingers of the cage. The unitary members are also prevented from moving toward each other by the arrangement of the pawl engagement members 21, sliding fingers 74 and the proximal end 82 of the spool. The engagement members must flex radially inwardly to slide over the pawls and close the anastomosis ring. However, the engagement members are prevented from flexing radially inwardly by the sliding fingers 74, which themselves cannot flex radially inwardly because they are opposed to the proximal end of the spool. Therefore, until the sliding fingers can flex radially inwardly, the engagement members cannot slide over the pawls and the anastomosis ring cannot be closed. The internal spring and transverse pin biases the cage in the distal direction to keep the lips 78 of the sliding fingers opposite to the engagement members and ensure that the anastomosis ring member remains open in the engagement position.

With the anastomosis ring secured on the adapter, the insertion device inserts the anastomosis ring into a natural body orifice and through a tubular body member. For purposes of this example, the insertion device is inserted through the mouth and into the esophagus. As the insertion device is being inserted, the trigger on the handle body is locked to prevent movement of the spool.

The anastomosis ring is positioned to approximately straddle the portion of the esophagus to be treated. The esophagus is severed and the diseased or cancerous portions of the esophagus are cut out and removed. The insertion device is adjusted, if necessary, to position the unitary members in the open ends 41 of the esophagus as shown in FIG. 3A. A purse string suture 43 is applied to each open end in a known manner. The suture is tightened to snugly draw each open end around the neck of its respective unitary member. At this point, the unitary members are ready to be closed to form the anastomosis ring.

To close the unitary members, the locking pin is removed from the trigger and the trigger is squeezed as shown in FIG. 4B to pull the control rod in the first, or proximal, direction. This action on the control rod retracts the spool into the collar as shown in FIG. 4A. The spool at first slides relative to the cage and moves the proximal end past the sliding fingers. This positions the truncated cone section 84 of the spool opposite to the sliding fingers. As the spool continues to retract, the abutting annular ring 88 on the spool contacts and drives the containing fingers on the cage in the first direction. The enlarged contact points 80 on the containing fingers in turn force the distal unitary member toward the proximal unitary member. This motion is made possible because the sliding fingers can now flex radially inwardly toward the truncated cone and allow the pawl engaging members to slide over the pawls. As the engaging members slide over the pawls, the anastomosis ring is locked in the closed position. The closed anastomosis ring secures therebetween the open ends of the esophagus to grow and heal together.

The trigger is then actuated in the opposite direction as shown in FIG. 5B to release the anastomosis ring adapter from the anastomosis ring. This action pushes the control rod and spool in the second, or distal, direction as shown in FIG. 5A. Initially, the spool slides axially in the distal direction relative to the cage. However, as the proximal end aligns itself with the sliding fingers, the outer periphery of the small washer 98 abuts the sliding fingers and moves the cage in the distal direction until the lips 78 on the sliding fingers engage the distal ends of the elongated slots 68. At this point, the cylindrical section 86 extends past the enlarged contact points on the containing fingers. As demonstrated in FIG. 4A, the cylindrical section biases the containing fingers radially outwardly when it is in contact with the enlarged contact points. However, when the cylindrical section extends past the enlarged contact points as shown in FIG. 5A, the containing fingers naturally flex radially inwardly toward a reduced diameter section 87 of the spool.

Figure 6:
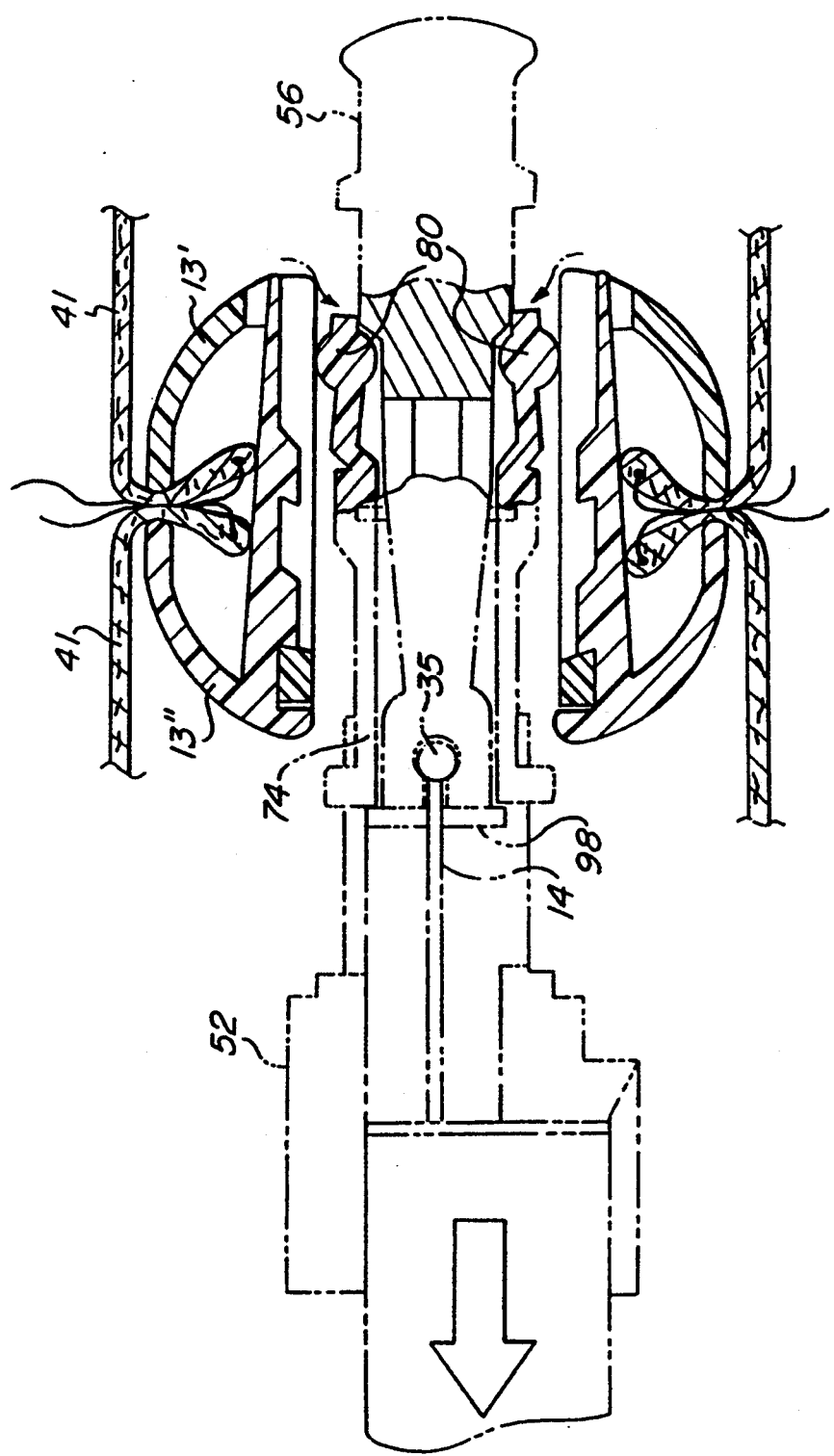
FIG. 6 is a cross-sectional view of the adapter being withdrawn from the anastomosis ring in accordance with the first embodiment of the present invention.

The entire insertion device can then be withdrawn through the body organ to release the adapter 16 from the anastomosis ring. As shown in FIG. 6, the containing fingers are biased radially inwardly such that the enlarged contact points do not engage the head of the distal unitary member. The adapter can then be withdrawn axially through the anastomosis ring.

FIGS. 10A through 16B illustrate in detail an endoscopic anastomosis ring insertion device in accordance with a second embodiment of the invention.

Figure 10A:
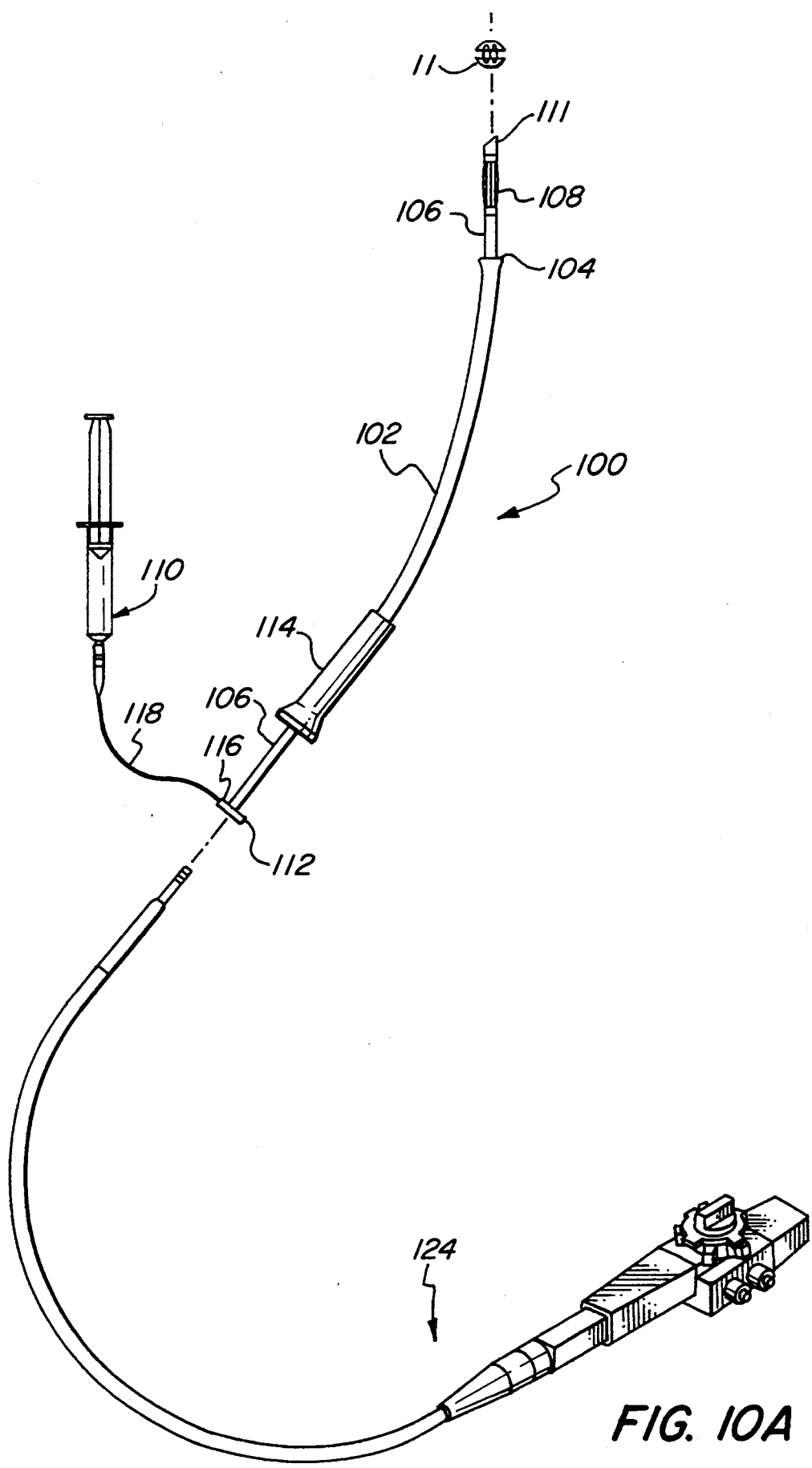
FIG. 10A is a perspective view of an endoscopic anastomosis ring insertion device in accordance with a second embodiment of the present invention, that includes a syringe and an independent endoscope.
Figure 10B:
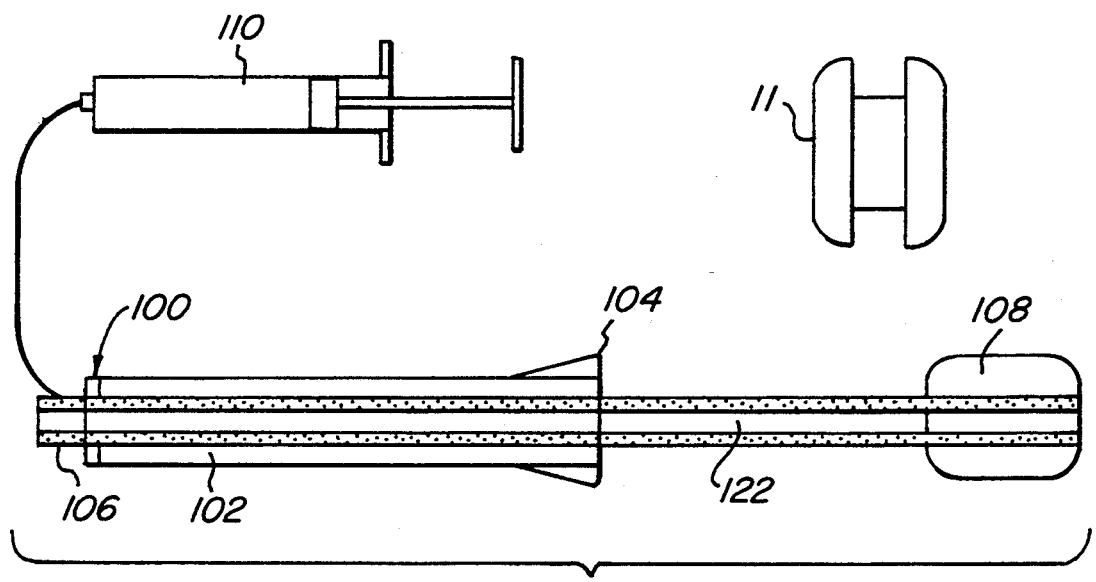
FIG. 10B is a diagrammatic view of the endoscopic insertion device in accordance with the second embodiment of the present invention.

FIGS. 10A and 10B show the basic components of the endoscopic insertion device 100. The insertion device includes a hollow outer sleeve 102 with a flared distal end 104 serving as a stop. An axially slidable obturator 106 operates as an actuator and extends entirely through the hollow sleeve. The obturator includes an inflatable cuff 108 at its distal portion. The cuff functions as an anastomosis ring adapter and is preferably puncture and rupture resistant. The cuff is designed to be inflated and deflated by a pressurized fluid medium, such as a saline solution, supplied from and withdrawn by a syringe 110. A distal tip 111 of the obturator is tapered to reduce the risk of injury when inserted through the tubular body member of the patient.

The proximal end of the obturator has a collar 112 for slidably manipulating the obturator within the outer sleeve. Similarly, a gripping handle 114 at the proximal end of the outer sleeve is used for manipulating the sleeve. Collar 112 includes a valve 116 for receiving a fluid line 118 for supplying the fluid medium to the cuff from syringe 110. The supply line can run the length of the obturator and into the cuff to supply and withdraw the fluid medium to inflate and deflate the cuff. Of course, other means for inflating and deflating the cuff are within the scope of this invention. A channel 122, as shown diagrammatically in FIG. 10B, is also provided in the obturator for receiving a conventional endoscope 124. The endoscope operates independently of the endoscopic insertion device of the present invention and can be used to guide the insertion device and also view closing of the anastomosis ring.

Operation of the endoscopic insertion device in accordance with the second embodiment involves a number of procedural steps described below. As a non-limiting example, description will be made of the device used to insert an anastomosis ring in the lower colon, or bowel section, of the intestines. An isolated view of the lower colon and the endoscopic insertion device of the second embodiment is provided in FIGS. 16A and 16B. Of course, the device can be used to insert an anastomosis ring in other tubular body members.

Figure 7:
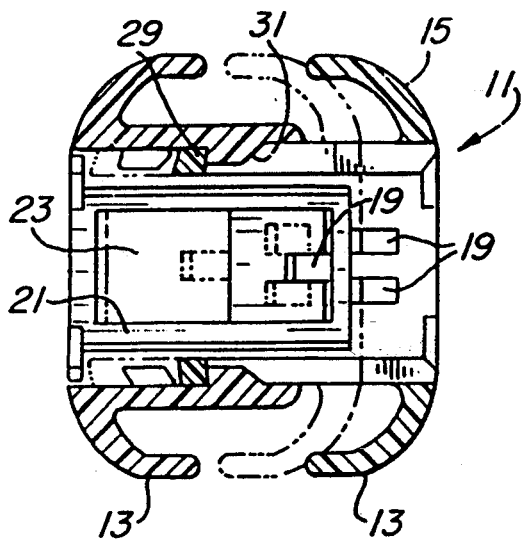
FIG. 7 is a cross-sectional side view of the anastomosis ring.
Figure 8:
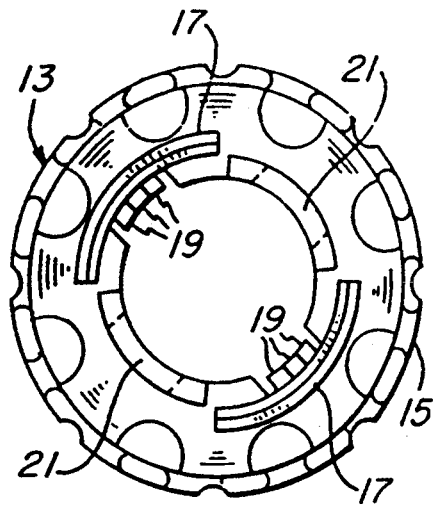
FIG. 8 is a bottom plan view of a unitary member of the anastomosis ring.
Figure 9:
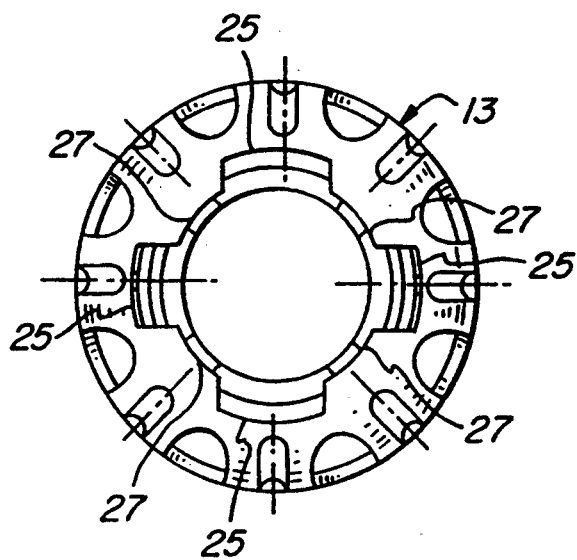
FIG. 9 is a top plan view of the unitary member of the anastomosis ring.
Figure 11C:
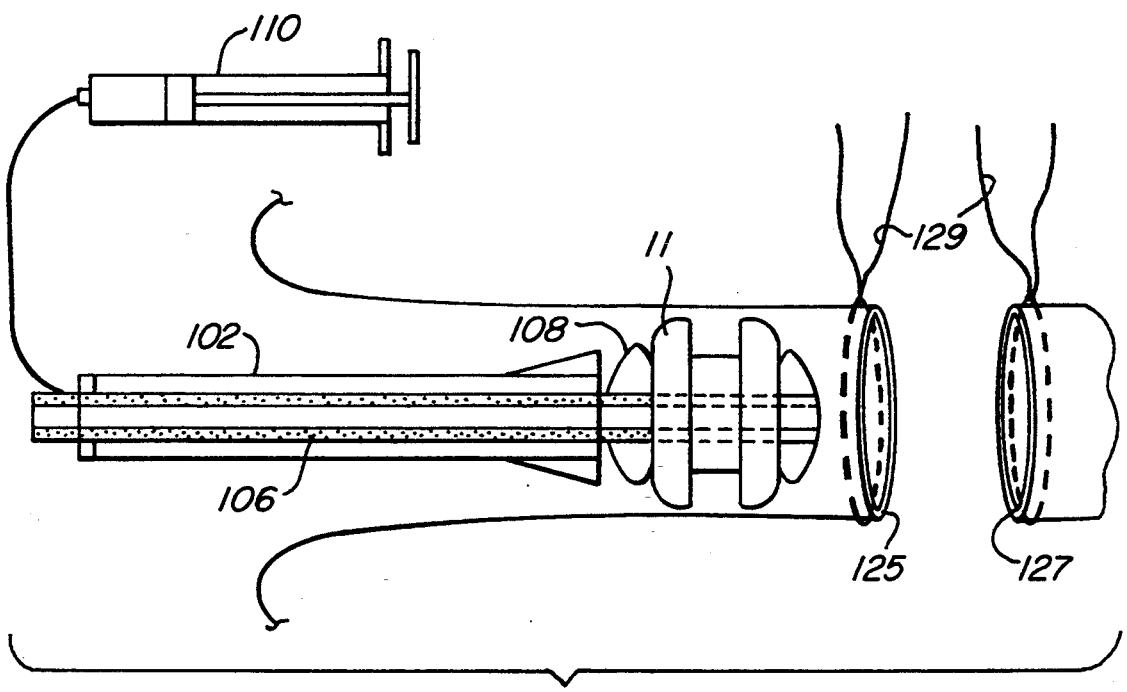
FIGS. 11C through 11G are diagrammatic views of the endoscopic insertion device in accordance with the second embodiment of the present invention illustrating steps of inserting and securing the anastomosis ring.
Figure 11B:
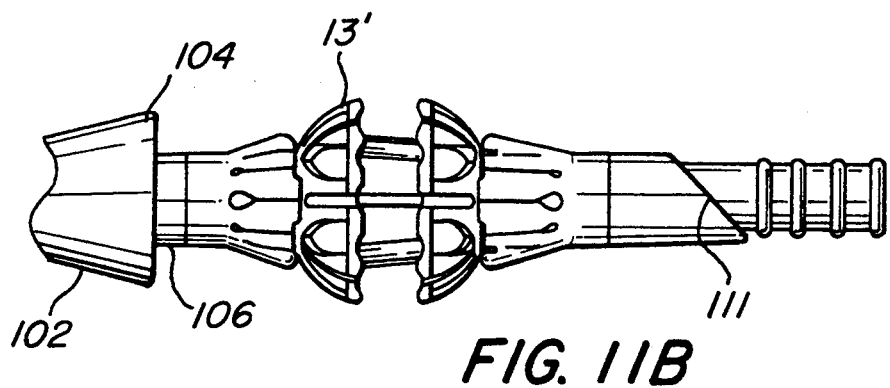
FIG. 11B is an enlarged view of the distal end of the endoscopic insertion device shown in FIG. 11A.
Figure 11A:
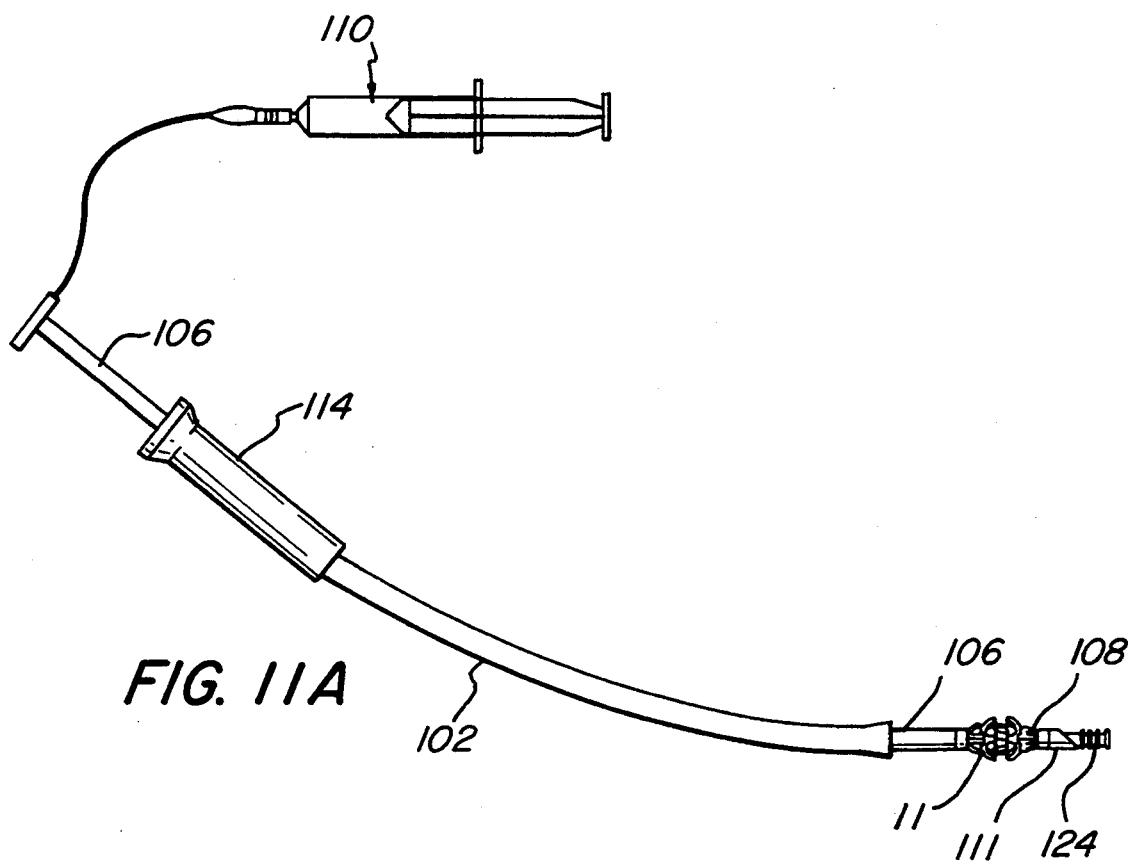
FIG. 11A is a side view of the endoscopic insertion device in accordance with the second embodiment of the present invention in a first position of use.
Figure 11D:
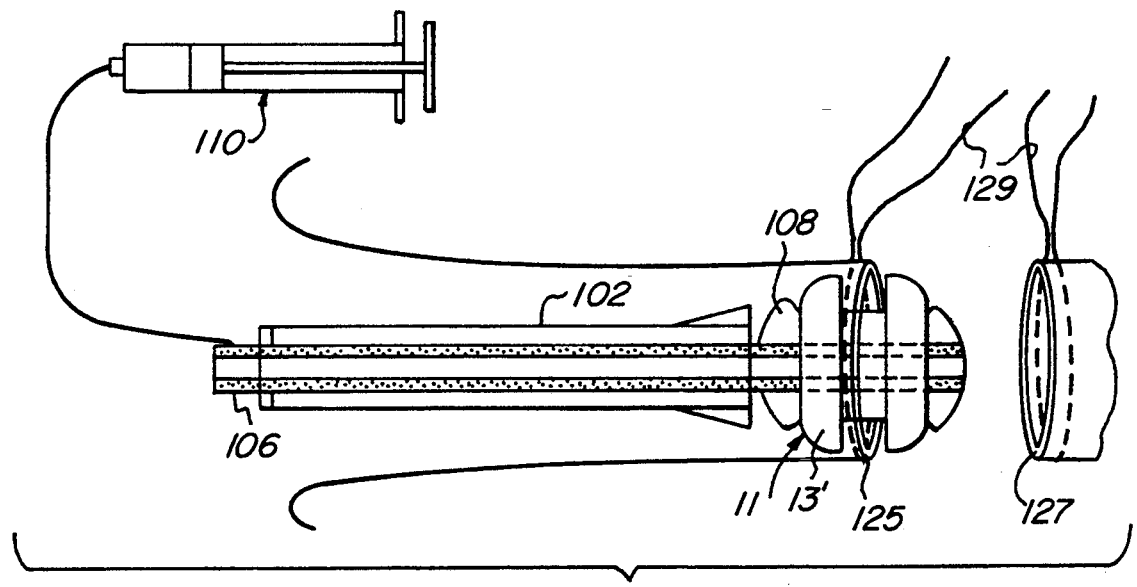
Figure 11E:
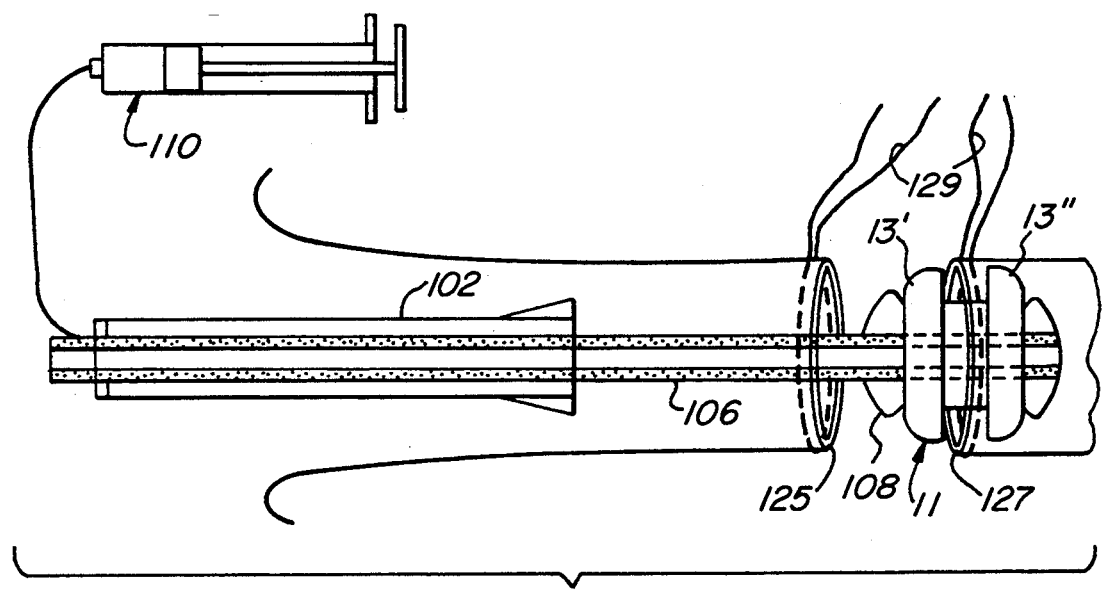
Figure 11F:
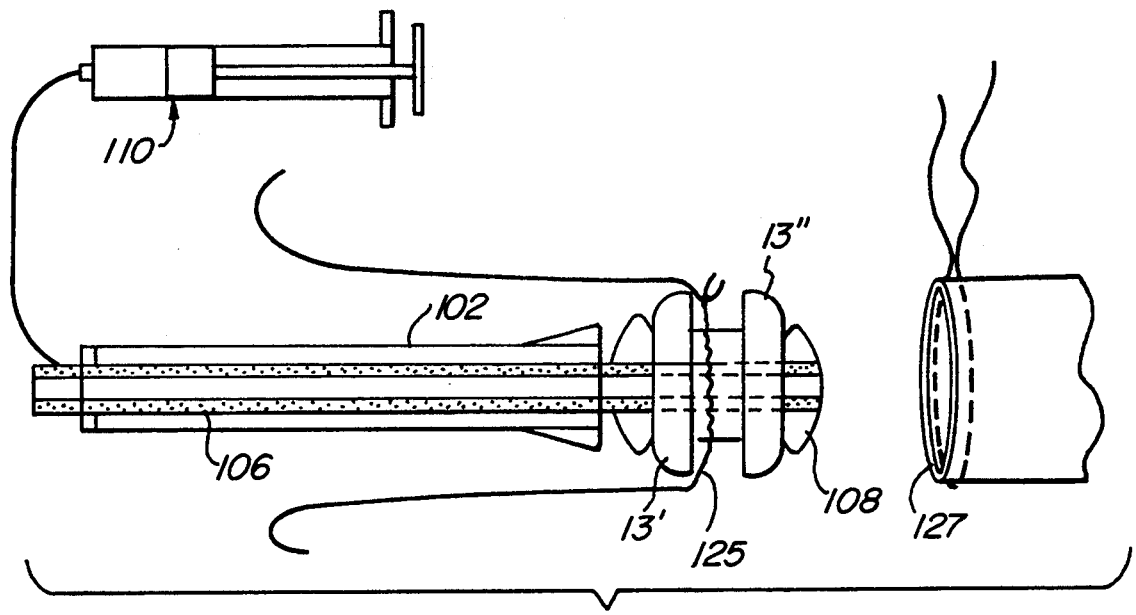
Figure 11G:
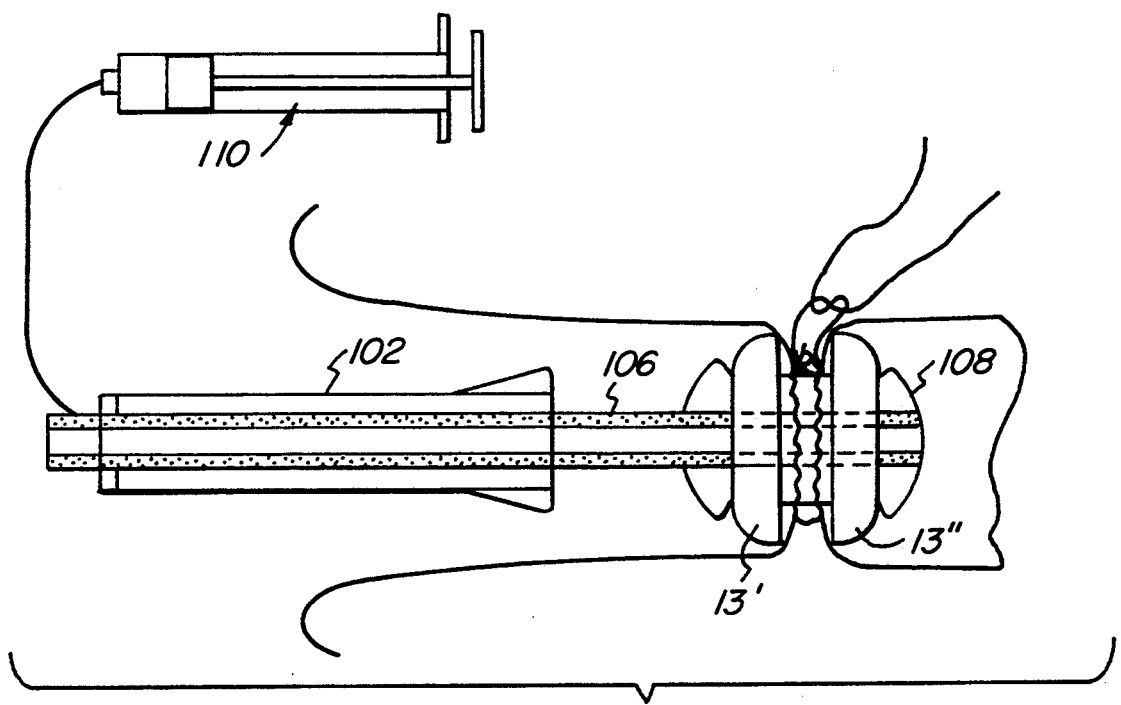

Initially, unitary members 13 are engaged to form anastomosis ring 11 as discussed earlier and shown in FIG. 7. The ring is then slipped over the distal end of obturator 106 and centered on deflated cuff 108. With reference now to FIGS. 11A and 11B, the cuff is partially inflated by receiving fluid from syringe 110 to restrict axial movement of the anastomosis ring. The insertion device is inserted into the intestinal tract as shown in FIG. 11C and advanced toward open opposite ends 125, 127 of the tubular body member, both of which have been prepared with a loose purse string suture 129. The first unitary member 13' is positioned to receive first open end 125 of the tubular body member as shown in FIG. 11D, and the purse string suture 129 is drawn tight to close the open end around that member 13' as shown in FIG. 11F. To conclude the first part of the surgical procedure, the insertion device is further advanced and the purse string 129 in second open end 127 is placed over the second unitary member 13" and secured as shown in FIG. 11G. Alternatively, the second unitary member 13" can be drawn tight first to the second open end of the tubular body member as shown in FIG. 11E.

Figure 12B:
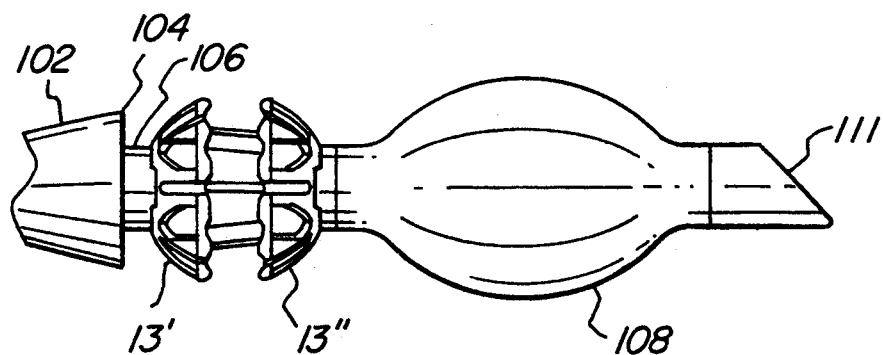
FIG. 12B is an enlarged side view of the distal end of the endoscopic insertion device shown in FIG. 12A.
Figure 12A:
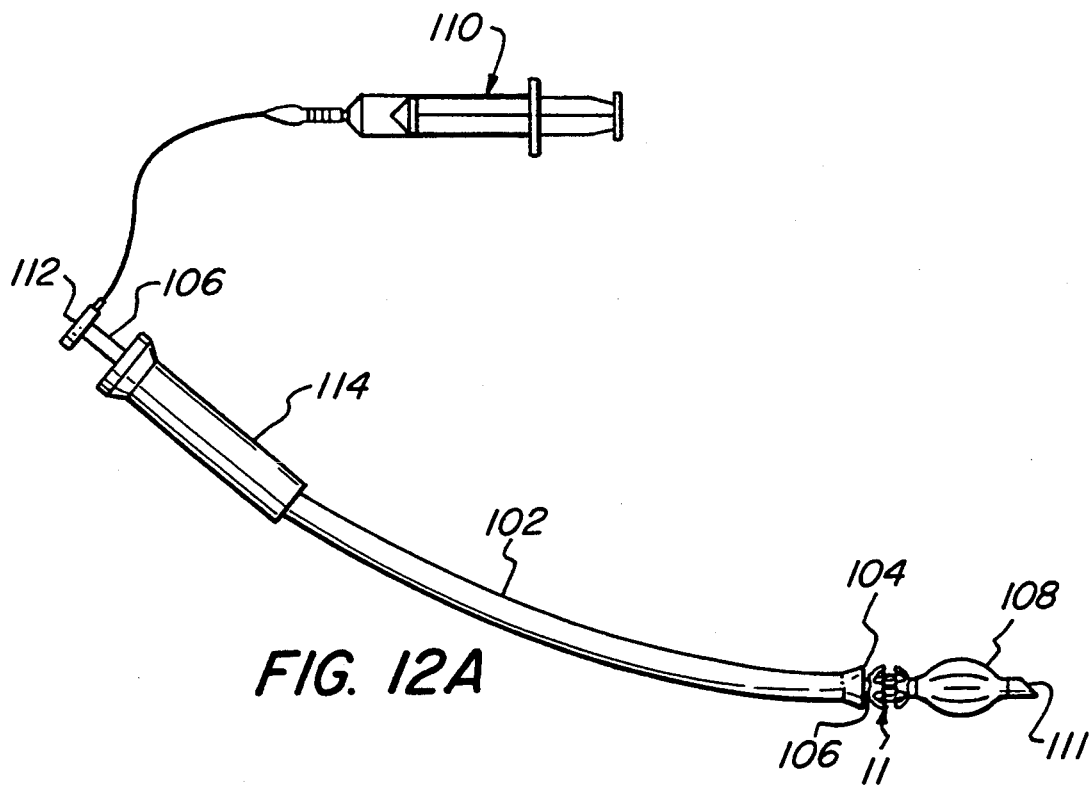
FIG. 12A is a side view of the endoscopic insertion device in accordance with the second embodiment of the present invention in a second position of use.
Figure 12C:
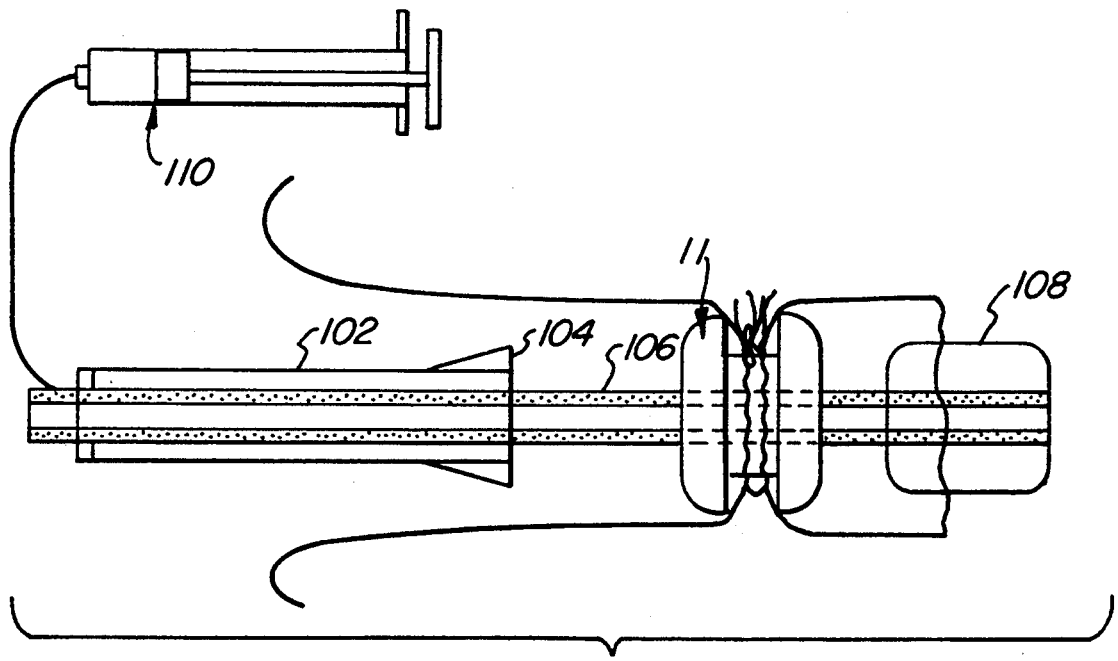
FIG. 12C is a diagrammatic view of the endoscopic insertion device in accordance with the second embodiment of the present invention illustrating a step of closing the anastomosis ring.
Figure 13C:
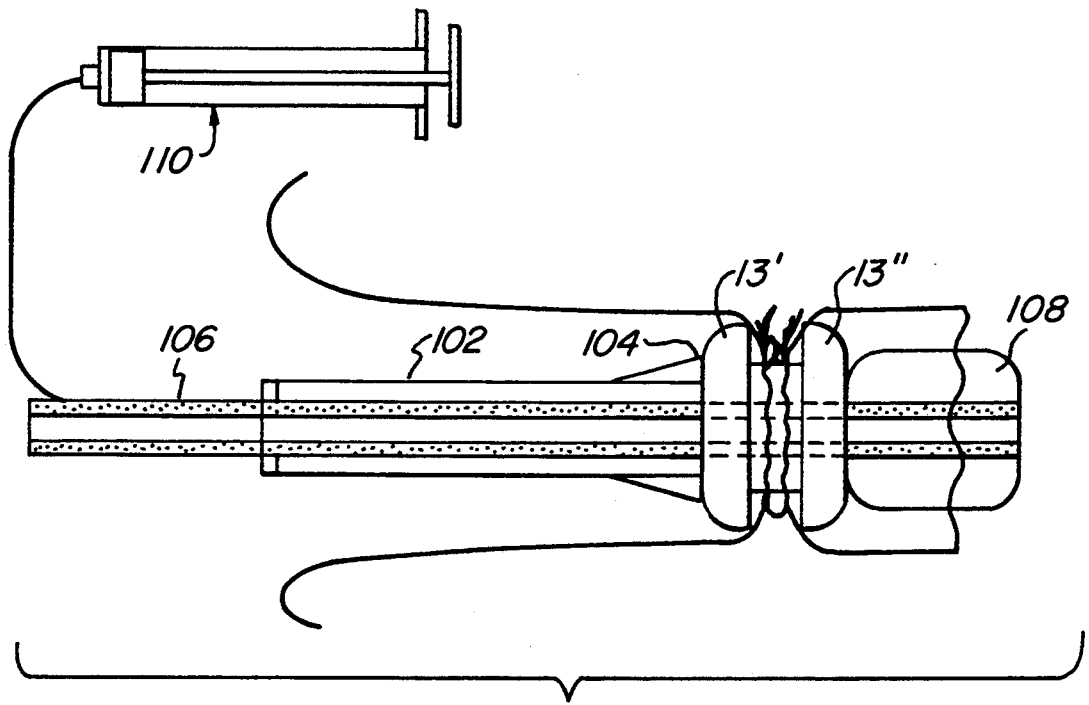
FIGS. 13C and 13D are diagrammatic views of the endoscopic insertion device in accordance with the second embodiment in the present invention illustrating additional steps in closing the anastomosis ring.
Figure 13B:
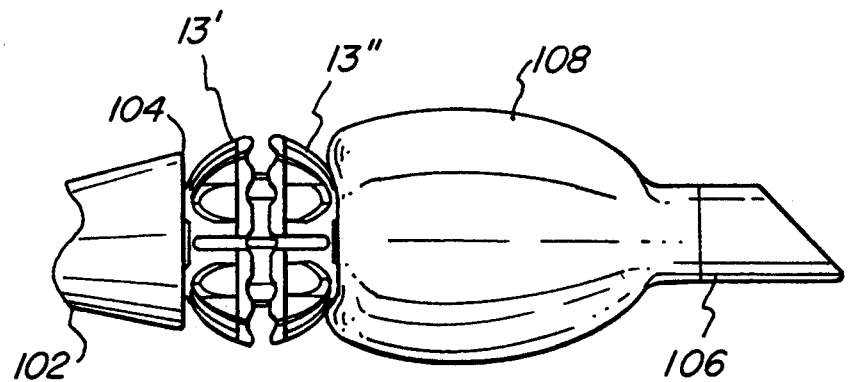
FIG. 13B is an enlarged side view of the distal end of the endoscopic insertion device shown in FIG. 13A.
Figure 13A:
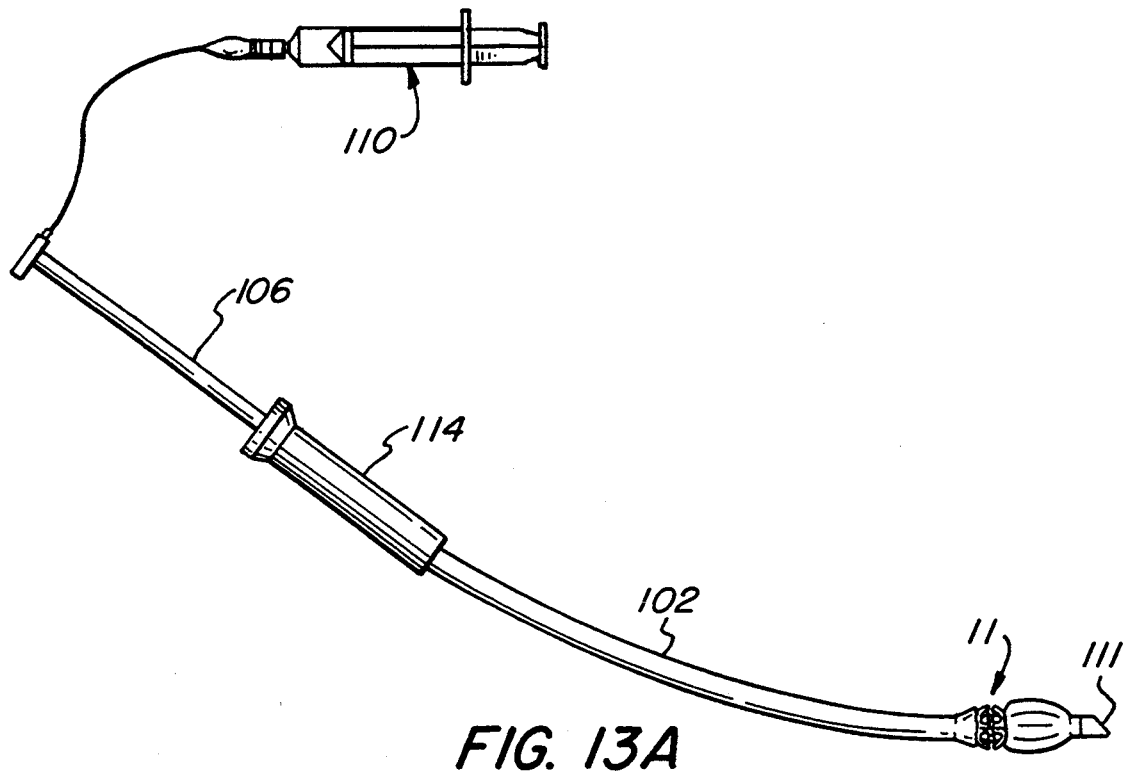
FIG. 13A is a side view of the endoscopic insertion device in accordance with the second embodiment of the present invention in a third position of use.
Figure 13D:
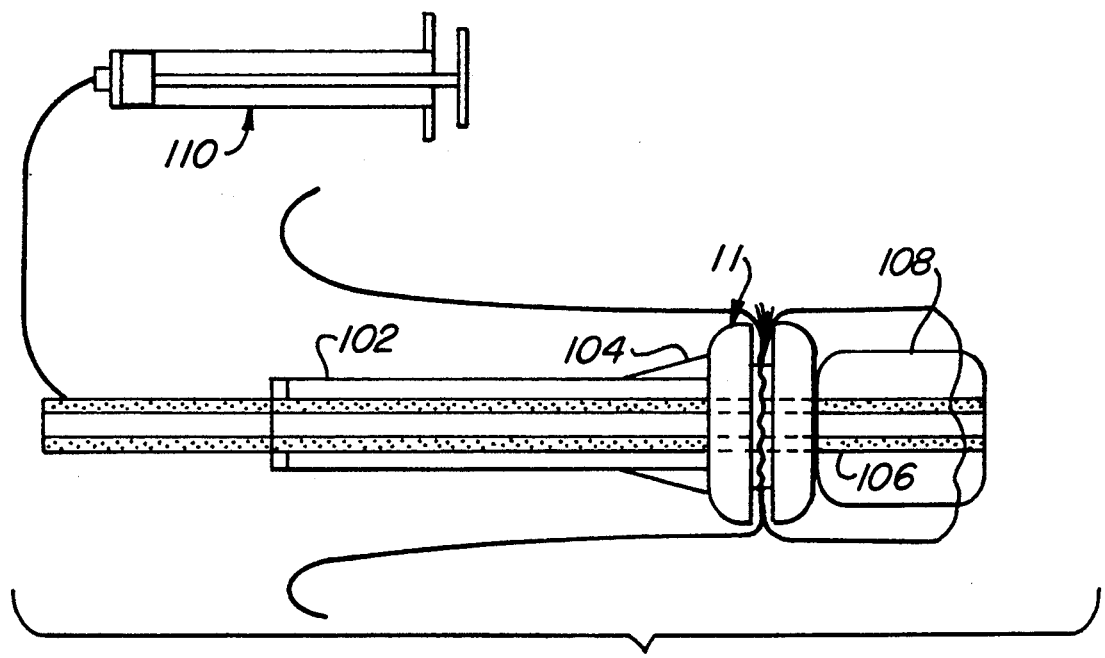

In the second part of the surgical procedure the cuff is deflated by withdrawing the fluid medium. The obturator is then distally advanced to position the cuff outside of the secured anastomosis ring. The cuff is then fully inflated by receiving the fluid medium as shown in FIGS. 12A and 12B, and is ready to be drawn in the proximal direction as shown in FIG. 12C. To close the anastomosis ring, obturator 106 is axially drawn proximally and outer sleeve 102 is relatively distally advanced to squeeze the unitary members 13' and 13" between inflated cuff 108 and stop 104, thereby closing the anastomosis ring. The inflated cuff is best seen in FIGS. 13A and 13B, and the ring closing steps are schematically illustrated in FIGS. 13C and 13D.

Figure 14:
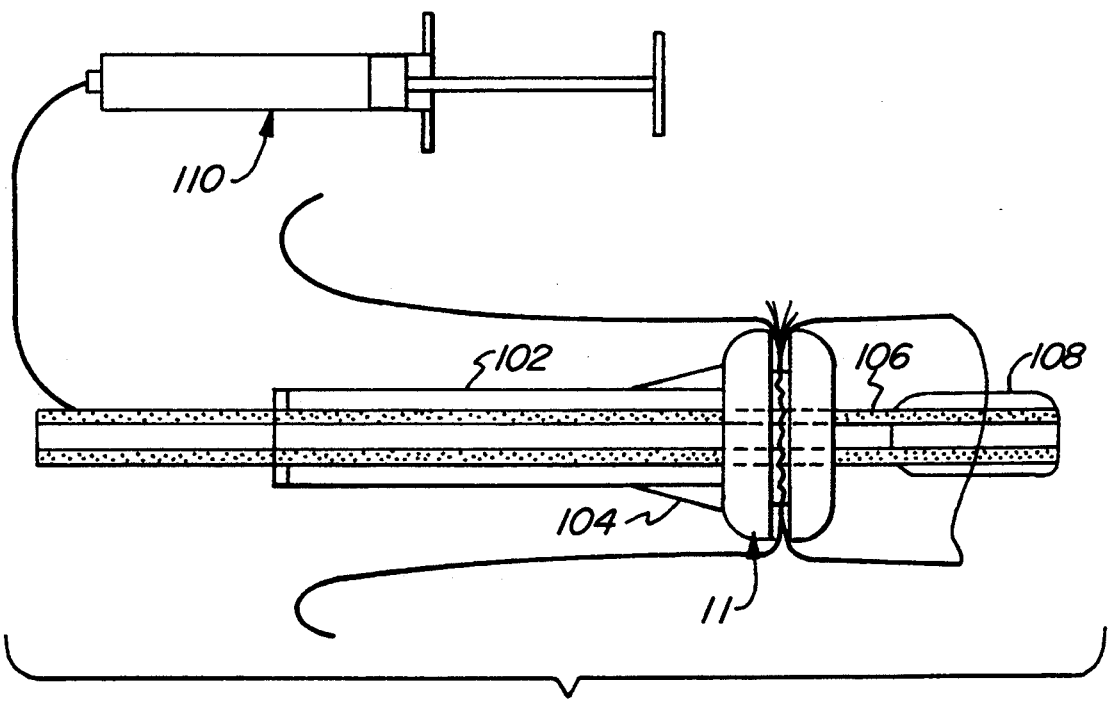
FIG. 14 is a diagrammatic view of the endoscopic insertion device in accordance with the second embodiment of the present invention illustrating a step of withdrawing the insertion device from the anastomosis ring.
Figure 15:
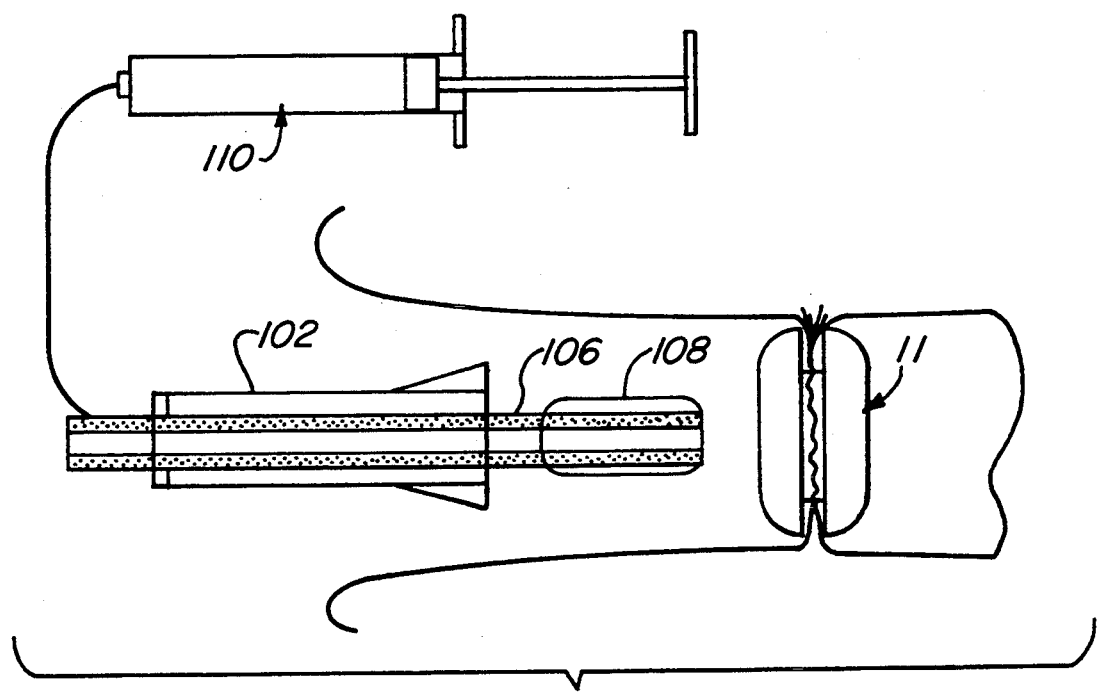
FIG. 15 is a diagrammatic view of the endoscopic insertion device in accordance with the second embodiment of the present invention illustrating an additional step of withdrawing the insertion device from the anastomosis ring.

The insertion device withdrawing steps may then be performed, whereby the obturator 106 is advanced slightly and the cuff 108 is deflated as shown in FIG. 14. The entire insertion device can be removed by withdrawing the obturator and outer sleeve as shown in FIG. 15, with the deflated cuff fitting through the central opening in the closed anastomosis ring. The intestinal anastomosis then is complete.

It will be appreciated that the present invention provides simple and effective structures for endoscopically positioning an anastomosis ring at a surgical site, permitting it to be secured to tubular tissue to be joined together. Thereafter, those structures can be easily manipulated to close the parts of the anastomosis ring thereby completing the tubular tissue anastomosis. Those structures can then be withdrawn from the anastomosis ring, the surgical site, and ultimately from the body.

Although specific embodiments of the present invention have been described above in detail, it will be understood that this description is merely for purposes of illustration. Various modifications of and equivalent structures corresponding to the disclosed aspects of the preferred embodiments in addition to those described above may be made by those skilled in the art without departing from the spirit of the present invention which is defined in the following claims, the scope of which is to be accorded the broadest interpretation so as to encompass such modifications and equivalent structures.

What is claimed is:

1. A method of performing anastomosis in a tubular body member with an anastomosis ring, which has an open configuration and a closed configuration, by using an endoscopic insertion device, which has an outer sleeve formed with a stop and an obturator axially movable within the outer sleeve, the device further having an inflatable cuff at its distal end; said method comprising the steps of:

positioning the anastomosis ring while in the open configuration on the cuff;

partially inflating the cuff to limit axial movement of the anastomosis ring;

inserting the cuff and the anastomosis ring into the tubular body member;

securing the open ends of the tubular body member to the anastomosis ring to position the open ends in confronting relation;

deflating the cuff and advancing the obturator to position the cuff distally in relation to the anastomosis ring;

inflating the cuff;

axially moving the sleeve and obturator relatively toward each other to abut the anastomosis ring between the inflatable cuff and the stop and to move the anastomosis ring to its closed configuration wherein the open ends of the tubular body member contact each other;

deflating the cuff; and axially withdrawing the insertion device from the tubular body member.

2. A method of performing anastomosis according to claim 1, further comprising the step of inserting an optical endoscope through an axial channel in the obturator to view the anastomosis.

3. A method of performing anastomosis according to claim 1, further comprising the step of using a syringe filled with a fluid medium to inflate and deflate the cuff.

4. A endoscopic insertion device for inserting an anastomosis ring having two unitary members into an anatomic tubular body member, comprising:

an anastomosis ring adapter having a cylindrical collar, a sliding cage mounted for axial movement within said collar, and a spool mounted for axial movement within said sliding cage, said cylindrical collar including a main section and a secondary section of a diameter smaller than said main section, with said secondary section having a plurality of elongated groves for receiving said sliding cage;

an endoscope connected at its distal end to said collar;

a handle assembly connected to a proximal end of said endoscope and having a pivotable trigger; and a control rod connected at a first end to said trigger and at a second end to said spool.

5. An endoscopic insertion device according to claim 4, said sliding cage including a plurality of sliding fingers extending in a first direction and a plurality of containing fingers extending in second opposite direction, each said sliding finger having an upturned lip for sliding in one of the elongated grooves in said secondary section, and each containing finger having an enlarged contact point for contacting the anastomosis ring.

6. An endoscopic insertion device according to claim 5, said spool including a cylindrical section for biasing said containing fingers radially outwardly to abut the anastomosis ring, and a reduced diameter section for permitting said containing fingers to flex radially inwardly to slide within the anastomosis ring.

7. An endoscopic insertion device according to claim 6, said spool further including a proximal end section for receiving the second end of said control rod, and further comprising a washer supported flush against said proximal end section for securing said control rod therein, wherein when said spool is driven in a distal direction, said washer abuts said sliding fingers to drive said sliding cage in the distal direction.

8. An endoscopic insertion device according to claim 7, said spool further including a truncated cone section disposed between said proximal end section and said reduced diameter section, wherein said truncated cone section permits said sliding fingers to flex radially inwardly and said proximal end section prohibits said sliding fingers from flexing radially inwardly.

9. An endoscopic insertion device according to claim 8, said spool further including an annular ring on said cylindrical section for abutting said containing fingers, wherein said annular ring abuts said containing fingers when said spool is actuated in a proximal direction.

10. An endoscopic insertion device for inserting an anastomosis ring having two unitary members into an anatomic tubular body member, comprising:

an anastomosis ring adapter having a cylindrical collar, a sliding cage mounted for axial movement within said collar, and a spool mounted for axial movement within said sliding cage, said spool further comprising biasing means for biasing said cage relative to said spool, said biasing means including an internal spring secured in said spool and a transverse pin connected to said spring and anchored in said cage;

an endoscope connected at its distal end to said collar;

a handle assembly connected to a proximal end of said endoscope and having a pivotable trigger; and a control rod connected at a first end to said trigger and at a second end to said spool.

11. An endoscopic insertion device for inserting an anastomosis ring having two unitary members into a tubular body member, comprising:

anastomosis ring adapter means for mounting two unitary members in an engaged position, said ring adapter means including slidable closing means for closing the anastomosis ring, and driving means for driving said closing means, said ring adapter means further including a cylindrical collar for receiving said closing means and said driving means, with said closing means sliding in an axial direction relative to said cylindrical collar and said driving means sliding in an axial direction relative to said closing means, said closing means further including a plurality of sliding fingers for limiting axial movement of said closing means within said cylindrical collar and containing fingers for abutting the anastomosis ring, and said driving means comprising a spool having a cylindrical section for biasing said containing fingers radially outwardly and a reduced diameter section for permitting said containing fingers to flex radially inwardly, wherein said containing fingers abut the anastomosis ring when they are biased radially outwardly by said cylindrical section;

inserting means for inserting said adapter means in a tubular body member; and actuating means for actuating said adapter means to close the anastomosis ring and release said adapter means from the anastomosis ring.

12. An endoscopic insertion device according to claim 11, said driving means further comprising a proximal end for preventing said sliding fingers from flexing radially inwardly and a truncated cone section for permitting said sliding fingers to flex radially inwardly.

13. An endoscopic insertion device according to claim 12, further comprising first connecting means for connecting said adapter means to said inserting means.

14. An endoscopic insertion device according to claim 13, further comprising second connecting means for connecting said adapter means to said actuating means.

15. An endoscopic insertion device according to claim 14, said actuating means including a handle assembly with a pivotable trigger and a control cable connected at one end to said trigger and at a second end to said adapter means.

16. An endoscopic insertion device according to claim 15, said actuating means further including a locking mechanism for locking said trigger in a locked position.

17. An endoscopic insertion device according to claim 16, wherein said inserting means comprises an endoscope.

* * * * *